United States Patent [19]
Aebischer et al.

[11] Patent Number: 5,092,871
[45] Date of Patent: Mar. 3, 1992

[54] ELECTRICALLY-CHARGED NERVE GUIDANCE CHANNELS

[75] Inventors: Patrick Aebischer, Barrington, R.I.; Paolo Dario, Livorno; Angelo Sabatini, La Spezia, both of Italy; Robert F. Valentini, Warwick, R.I.

[73] Assignee: Brown University Research Foundation, Providence, R.I.

[21] Appl. No.: 600,021

[22] Filed: Nov. 30, 1990

Related U.S. Application Data

[63] Continuation of Ser. No. 272,555, Nov. 17, 1988, abandoned, which is a continuation-in-part of Ser. No. 25,529, Mar. 13, 1987, abandoned.

[51] Int. Cl.$^5$ .......................... A61B 11/00; A61F 2/04
[52] U.S. Cl. ............................................ 606/152; 623/12
[58] Field of Search .................. 606/76, 152, 153; 623/12; 128/419 F

[56] References Cited

U.S. PATENT DOCUMENTS

| | | | |
|---|---|---|---|
| 3,925,339 | 12/1975 | Ishii et al. | 260/92.1 |
| 3,968,790 | 7/1976 | Fukada et al. | 606/76 |
| 4,268,653 | 5/1981 | Uchidoi et al. | 526/255 |
| 4,668,449 | 5/1987 | Soni et al. | 264/22 |

OTHER PUBLICATIONS

Fukada in *Mechanisms of Growth Control*, "Piezoelectricity of Bone and Osteogenesis by Piezoelectric Films", R. O. Becker, C. C. Thomas (eds.), Springfield, Md. (1981) pp. 192–210.

De Rossi et al. (1983) Am. Soc. Artificial Organs 5:1–11.

*Primary Examiner*—Stephen C. Pellegrino
*Assistant Examiner*—Gary Jackson
*Attorney, Agent, or Firm*—Thomas J. Engellenner; Ann-Louise Kerner

[57] ABSTRACT

A medical device is disclosed for use in regenerating a severed nerve, including a tubular, biocompatible, electrically-charged membrane or guidance channel, having openings adapted to receive the ends of the severed nerve and defining a lumen through which the nerve can regenerate. The electrically-charged membrane can further include a polymeric electret material that is electrically poled. A method for repairing a severed nerve is also disclosed and includes placing severed nerve ends in proximity to each other within the lumen of the guidance channel of the present invention and securing the nerve ends to the device.

7 Claims, 3 Drawing Sheets

ELECTRICALLY-CHARGED NERVE GUIDANCE CHANNELS

CROSS REFERENCE TO RELATED APPLICATION

This is a continuation of application Ser. No. 272,555, filed Nov. 17, 1988, now abandoned, which is a continuation-in-part of U.S. patent application Ser. No. 025,529, filed Mar. 13, 1987, now abandoned the disclosure of which is incorporated herein by reference.

BACKGROUND OF THE INVENTION

The technical field of this invention concerns medical devices useful for the repair of severed nerves and methods for fabricating and using such devices for nerve repair.

The problem of repairing severed nerves is a long-standing one that has plagued surgeons for over a hundred years. Despite advances in microsurgical techniques, a patient's recovery from a serious wound is often limited by a degree of nerve damage which cannot be repaired. The replanting of amputated fingers and limbs is especially limited by poor nerve regeneration.

When a nerve is severed, the functions supplied by that nerve, both motor and sensory, are lost. The appendages of the nerve cells, or axons, in the distal regions of the severed nerve, or those areas furthest from the spinal cord, degenerate and die, leaving only the sheaths in which they were contained. These, too, degenerate with time. The axons in the proximal stump that remain connected to the spinal cord or dorsal root ganglion also suffer some degeneration.

However, degeneration generally does not proceed to the death of all of the nerve cell bodies. Moreover, if the injury occurs far enough from the nerve cell bodies, regeneration will occur. Axonal sprouts will appear from the tip of the regenerating axon. These sprouts grow distally and attempt to reenter the intact, neurilemmal sheaths of the distal portion of the severed nerve. If entry is successfully made, axonal growth will continue down these sheaths, and function will eventually be restored.

In the conventional approach to nerve repair, an attempt is made to align the cut ends of the fascicles (nerve bundles within the nerve trunk). A similar approach is taken with smaller nerves. In either case, the chief hazard to the successful repair is the trauma produced by the manipulation of the nerve ends and the subsequent suturing to maintain alignment. The trauma appears to stimulate the growth and/or migration of fibroblasts and other scar-forming, connective tissue cells. The scar tissue prevents the regenerating axons in the proximal stump from reaching the distal stump to reestablish a nerve charge pathway. The result is a permanent loss of sensory or motor function.

Various attempts have been made over the years to find a replacement for direct (i.e., nerve stump-to-nerve-stump suturing). Much of the research in this field has focused on the use of "channels" or tubular prosthesis which permit the cut ends of the nerve to be gently drawn into proximity and secured in place without undue trauma. It is also generally believed that such channels can also prevent, or at least retard, the infiltration of scar-forming, connective tissue.

For example, the use of silastic cuffs for peripheral nerve repair was reported by Ducker et al. in Vol. 28, *Journal of Neurosurgery*, pp. 582-587 (1968). Silicone rubber sheathing for nerve repair was reported by Midgley et al. in Vol. 19, *Surgical Forum*, pp. 519-528 (1968) and by Lundborg et al. in Vol. 41, *Journal of Neuropathology in Experimental Neurology*, pp. 412-422 (1982). The use of bioresorbable polyglactin mesh tubing was reported by Molander et al. in Vol. 5, *Muscle & Nerve*, pp. 54-58 (1982). The use of semipermeable acrylic copolymer tubes in nerve regeneration was disclosed by Uzman et al. in Vol. 9, *Journal of Neuroscience Research*, pp. 325-338 (1983). Bioresorbable nerve guidance channels of polyesters and other polymers have been reported by Nyilas et al. in Vol. 29, *Transactions Am. Soc. Artif. Internal Organs*, pp. 307-313 (1983) and in U.S. Pat. No. 4,534,349 issued to Barrows in 1985.

Despite the identification of various materials which can serve as nerve guidance channels, the results of research to date have revealed significant shortcomings in such prosthesis. For example, some of the materials identified above have lead to inflammatory reactions in the test animals, and have failed to exclude scar tissue formation within the channels. The total number of axons, the number of myelinated axons, the thickness of the epineurial, and the fascicular organization of nerves regenerated within guidance channels are all typically less than satisfactory and compare poorly with the original nerve structure of the test animals. Moreover, the loss of sensory or motor function is still the most common outcome of such laboratory experiments.

Exogenously applied electrical fields have been shown to enhance PNS regeneration in experimental animals. Both the extent of neurite outgrowth in vitro and nerve regeneration in vivo following transection injury, have been shown to be influenced by direct DC stimulation or by pulsed electromagnetic fields. For example, galvanotropic currents produced by electrode cuffs, connected to an extracorporeal power source, and fitted to a silicone channel, have been used to enhance PNS regeneration in vivo (Kerns et al. Vol. 12, *Soc. Neurosci. Abstr.* pp. 13 (1986)). However, such devices are bulky, typically requiring an external power supply and electrode leads penetrating through the skin and, therefore, are difficult to maintain.

There exists a need for more effective nerve guidance channels which would enable the restoration of motor and/or sensory function. Materials and methods for nerve repair that would minimize surgical trauma, maximize the distance over which nerves will regenerate and the amount of neural tissue regrowth, prevent interference with nerve growth by scar tissue, and improve the chances for successful recovery of sensory or motor function. This would satisfy a long-felt need in this field.

In U.S. patent application Ser. No. 025,529, the present applicants have disclosed that nerve guidance channels can be formed from materials that are capable of generating electrical charges on their surfaces. These electrical charges apparently augment the ability of axons to bridge the gap between the proximal and distal nerve stumps. In particular, parent application Ser. No. 025,529 discloses the use of polyvinylidene difluoride (PVDF) which is subjected to a strong, electric field to create strong, permanent dipole moments throughout the material.

SUMMARY OF THE INVENTION

The present application discloses improved, electrically-charged, medical prosthesis for use as guidance channels in the repair of severed or otherwise damaged nerves. Additional electret materials are disclosed which can be poled in accordance with the teachings of U.S. Ser. No. 025,529, or by alternative techniques, to obtain nerve guidance channels displaying quasi-permanent, surface charges. The devices include a tubular structure composed of a polymeric, electret material adapted to receive the ends of a severed nerve and defining a lumen through which axons can be regenerated. The electret materials generate static electrical charges which greatly augment the ability of the severed nerve ends to bridge the gap therebetween.

The term "nerve" is used herein to mean both monofascicular and polyfascicular nerves. The same general principals of regeneration within the nerve guidance channels of the present invention are applicable to both. The term "electret", as used herein, is intended to broadly encompass natural materials and synthetic materials displaying surface electrical charge storage capabilities.

The guidance channels of the present invention may be negative or positively poled (or a combination thereof) and may have electrical charges on the inner or outer surface of the tubular membrane (or both). A preferred electret material is polytetrafluoroethylene (PTFE).

The invention further encompasses methods of repairing a severed nerve. In these methods, the cut ends of the nerve are placed into the openings of the nerve guidance channel and secured therein.

Methods of fabricating the device useful in regenerating a severed nerve are also disclosed. These include producing the tubular, polymeric, electret material, and then poling it to establish the accumulation of negative or positive charges on the inner or outer surface of the channel.

The invention will next be described in connection with certain preferred embodiments; however, it should be clear that various changes, additions and subtractions can be made by those skilled in the art without departing from the spirit or scope of the invention. For example, although the nerve guidance channels described in the examples below are generally tubular in shape, it should be clear that various alternative shapes can be employed. The lumens of the guidance channels can be oval or even square in cross-section. The guidance channels can also be constructed from two or more parts which are clamped together to secure the nerve stumps. Moreover, polymeric, electret sheet materials can be employed and formed into channels in situ. In such a procedure, the nerve stumps can be placed on top of the sheet and then secured thereto by sutures, adhesives, or friction. The sheet can then be wrapped around the nerve segments, and the resulting channel closed by further sutures, adhesives, or friction.

BRIEF DESCRIPTION OF THE DRAWINGS

The foregoing and other objects of the present invention, as well as the various features thereof, and the inventions thereof, may be more fully understood from the following description when read together with the accompanying drawing in which.

DETAILED DESCRIPTION

Figure 1:
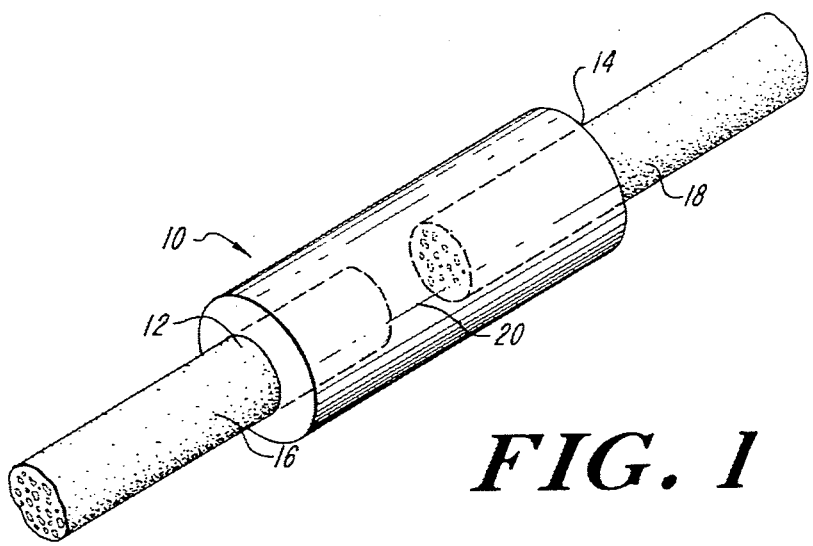
FIG. 1 is a schematic representation of a nerve guidance channel of the present invention.
Figure 2A:
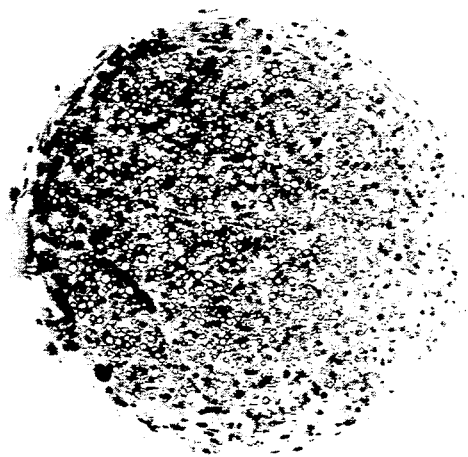
FIG. 2 is a series of electron micrographs of toluidine blue-stained transverse sections of nerves regenerated at the midpoint of unpoled (A), negatively poled (C), and positively poled (E) PTFE channels four weeks postimplantation. (B), (D), and (F) are higher power micrographs of the nerves shown at lower power in (A), (C), and (E), respectively.
Figure 2C:
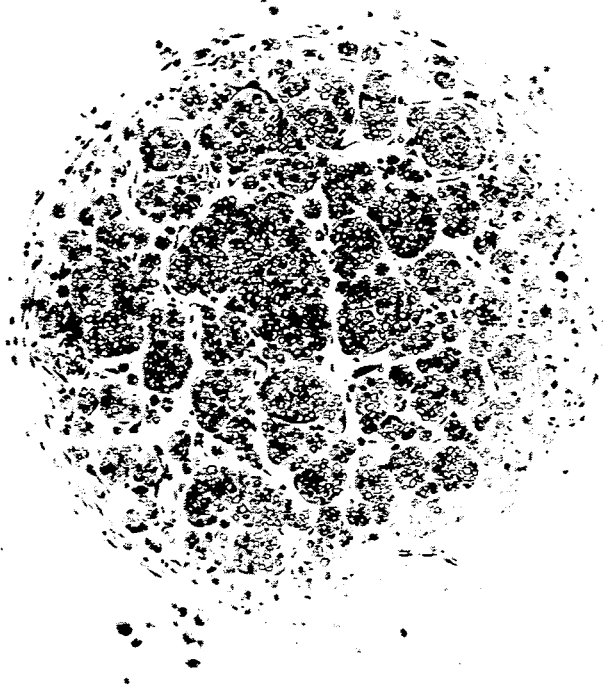
Figure 2E:
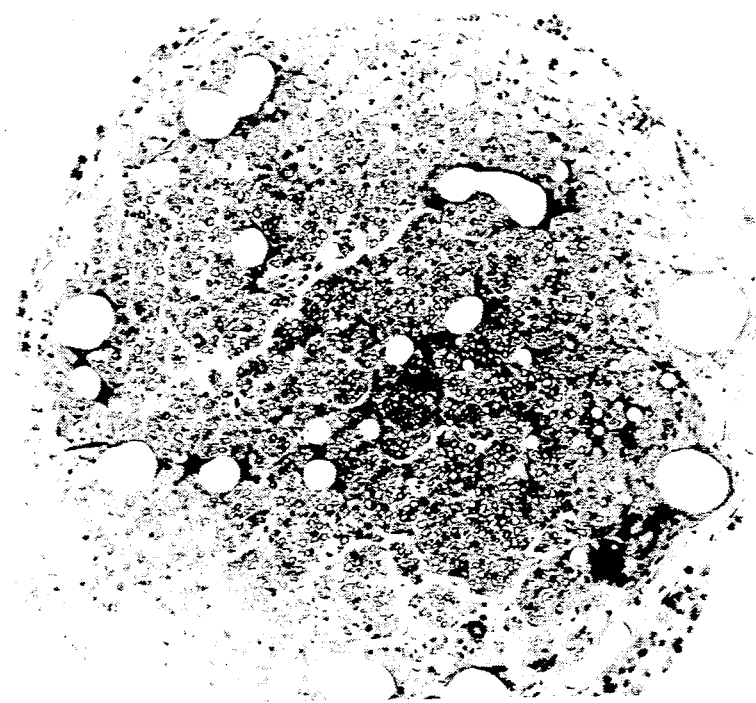
Figure 2F:
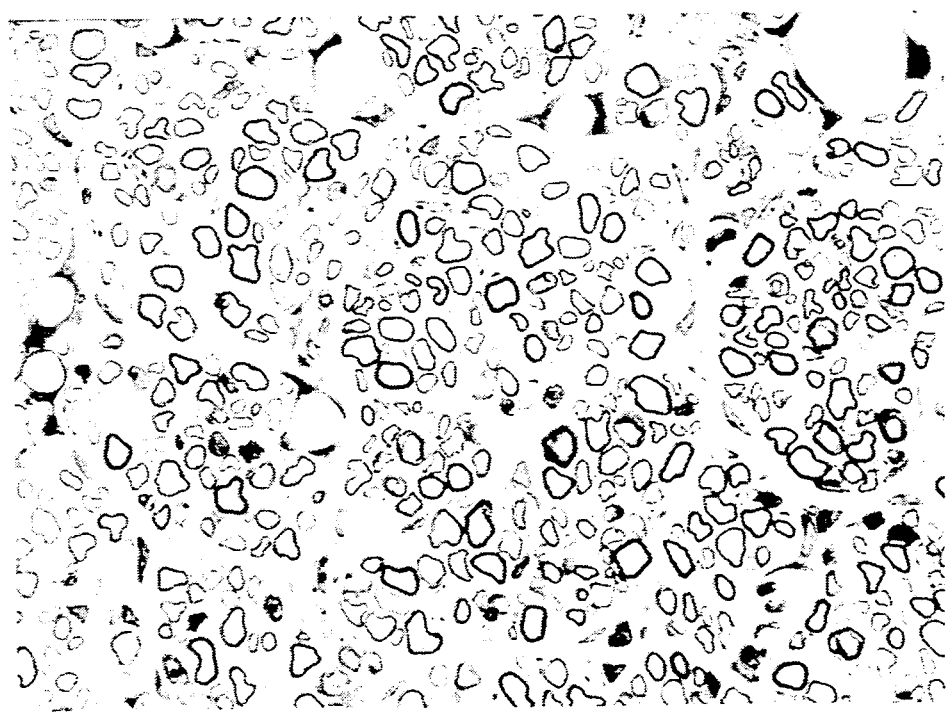
Figure 2B:
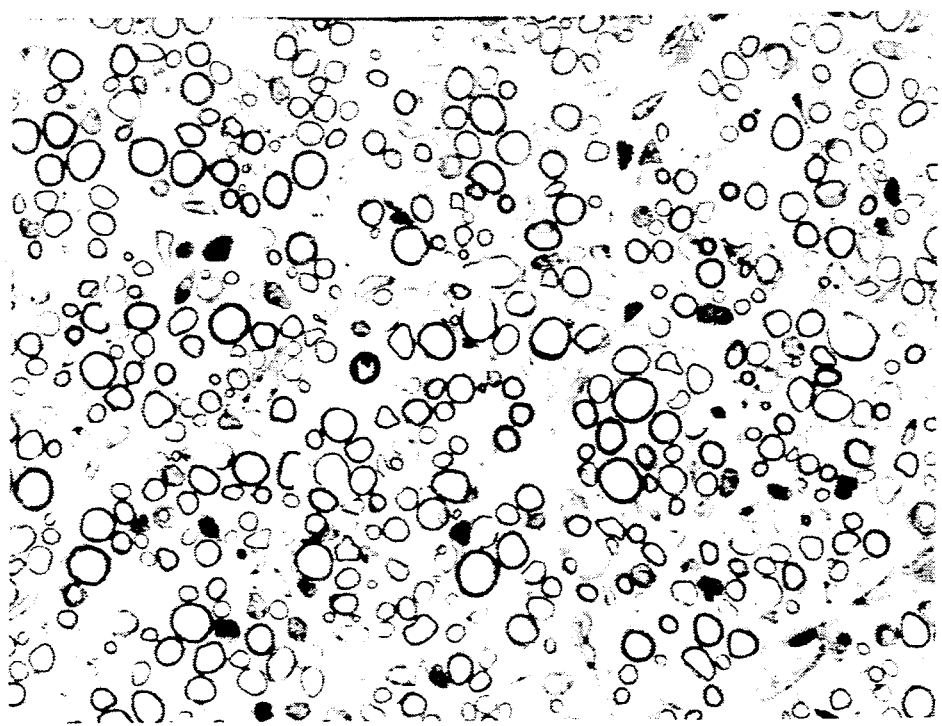
Figure 2D:
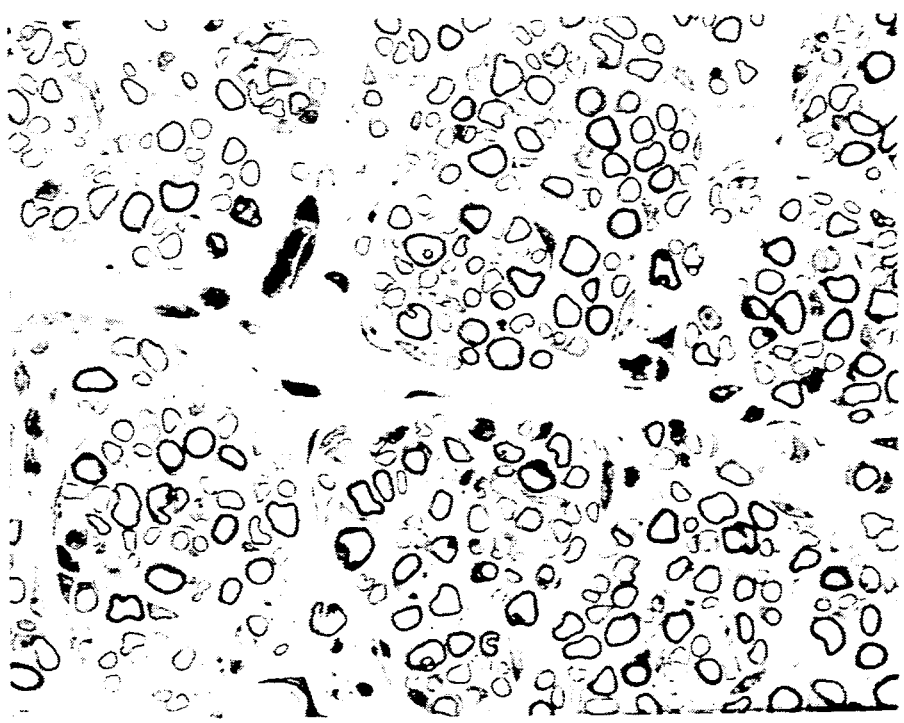

The nerve guidance channels of the present invention, an example of which is shown in FIG. 1, are composed of a tubular membrane 10 having openings 12 and 14 adapted to receive severed nerve ends 16 and 18 into lumen 20.

Preferably, the thickness of the membrane wall ranges from about 0.05 to about 1.0 millimeters (mm). Lumen 8 typically has a diameter which can vary from about 0.5 mm to about 3 centimeters (cm), depending upon the size of nerve to be repaired.

The membrane is composed of one of a class of electret materials which can be endowed with a transient or static electrical charge due to their physico/chemical properties. Electrets are attractive for in vivo applications since they can be fabricated from biocompatible polymers and can produce electrical charges without an external power source.

To generate and contain these trapped charges, the electret materials of the present invention are preferably poled. Poling can be performed during manufacture or prior to use and may result in negative or positive charge accumulation on the inner or outer surface of the tubular membrane.

One class of electrets are piezoelectric materials which depend primarily on dynamic mechanical deformation in order to produce transient charge generation on their surface. Charge generation is due to the presence of stable molecular dipoles found throughout the bulk of the polymer. For example, piezoelectric polyvinylidene fluoride (PVDF) guidance channels have been shown to enhance nerve regeneration as compared to identical but non-piezoelectric PVDF tubes (Aebischer et al., Vol. 436, *Brain Res.* pp. 165–168 (1987); and copending patent application Ser. No. 025,529). The effects observed are attributed to the transient charges generated as a consequence of random animal movements deforming the channel.

However, because charge generation in piezoelectric material is dependent upon movement, it is not as reliable as those charges generated independently of movement. Without any external stimulation, a non-piezoelectric electret material exhibits a charge storage mechanism consisting primarily of monopolar charges entrapped throughout the polymer. The distribution and stability of this static surface charge are related to the method of fabrication (including poling).

Electret materials useful in the present invention include polytetrafluoroethylene (PTFE), polyvinylchloride, polyethylene, polyamides, polymethyl methacrylate, polypropylene, polyethylene terapthalate, or mixtures thereof. One particularly preferred electret material for nerve guidance channels is PTFE.

In one embodiment of the invention, nerve guidance channels include positively poled electret material, having a preferable average charge density ranging from about 1 to 100 nanoColoumbs per square centimeter ($nC/cm^2$) and, more preferably, about 21 ($nC/cm^2$). In alternative embodiments of the invention, nerve guidance channels consist of negatively poled electret material, having a preferable average charge density of from about 5 to 30 $nC/cm^2$, with 9 $nC/cm^2$ being a preferred value.

In addition, the lumen of the device may be "seeded" or prefilled with a substance that protects, soothes, nutures, and/or enhances nerve growth therethrough. The membrane is designed to be impermeable to such substances so that they remain within the walls or lumen of the device and, hence, in close contact with the regenerating nerve ends. Useful substances may include, for example, a saline solution or a matrix material, such as laminin, collagen, fibrin, glycosaminoglycan, biologically active factors, such as nerve growth factors and enhancers, or mixtures thereof. Alternatively, the lumen may be seeded with glial cells, such as Schwann cells which are known to stimulate and protect neuronal appendages.

Other useful substances include active factors or any diffusible substances with bioactivity that stimulates nerve growth. Useful active factors include, for example, second messenger substances, such as cAMP, or membrane-permeable permanent cAMP analogs, such as 8-bromo cAMP or chlorophenylthio cAMP. A "second messenger" substance is one that initiates a cellular response to a specific signal external to that cell. Second messenger inducers such as forskolin are also useful. In addition, growth factors, such as nerve growth factor, brain-derived growth factor, fibroblast growth factor, and mixtures thereof, are also useful active factors.

The invention further encompasses methods of repairing a severed nerve. In these methods, the nerve guidance channels of the present invention, as described above, are used by locating the severed nerve ends and selecting and providing an appropriately-sized, tubular device for the repair. The cut ends of the nerve are then gently drawn into channel by manual manipulation or suction, placed in optimal proximity and then secured in position without undue trauma by sutures through the channel, or by a biocompatible adhesive (e.g., fibrin glue) or by frictional engagement with the channel. The channel is then situated in the general in vivo location of the nerve. Antibiotics can be administered to the site, and the wound is then closed. The nerve repair method of the present invention may further include splitting of the channel along a line of weakness and removing it from the nerve ends after they have regenerated and joined.

With time, implanted nerve guidance channels of the present invention have been found to contain regenerated nerve cables. In particular, channels composed of poled electret material were observed to enhance the regeneration of more morphologically normal myelinated nerves when compared with channels composed of unpoled materials.

The invention will next be described in connection with the following examples and experiments.

EXAMPLE 1

Polytetrafluoroethylene (PTFE) tubes were submitted to a corona poling procedure in order to inject electrical carriers into them. A brass wire fitted into the lumen of the tube was used as a reference electrode. A circumferential array of regularly-spaced, steel needles connected to a high voltage D.C. power supply, at a distance of 2 mm from the outer wall of the tube, served to generate the high intensity electric field required for electret preparation. The outer electrode array was connected to the positive output of the power supply with the inner electrode grounded during positive corona discharge, polarities were reversed for negative corona discharge.

The corona poling was performed at a relatively high temperature (150° C.) in order to obtain electrets with high charge storage capabilities. At high temperatures, it is possible for the charge carriers to achieve greater depths of penetration into the polymer bulk, although penetration depth rarely exceeds a few microns. The applied voltage was gradually increased to a level of 14 KV and maintained at that voltage for 20 min. at 150° C.

The net surface charge density on the outer surface of each electret tube was measured using an induction-based method. A capacitative probe was placed 2 mm from the outer surface of the electret tube and connected to an electrometer (Keithley 610 C, Cleveland, OH). When exposed to the electric field produced by the electret, the probe acquires a charge derived from the capacitance at the input of the electrometer. The meter voltage is thus directly related to the quantity of charge trapped in the electret. The average charge density measured for positively poled tubes was 21 nanoCoulombs per square centimeter ($nC/cm^2$); and for negatively poled tubes, it was 9 $nC/cm^2$. The different charge density achieved in otherwise identical PTFE samples can be attributed to the limited penetration of negative charges into PTFE films. All tubes were cleaned and sterilized identically prior to implantation.

EXAMPLE 2

The nerve guidance channels were then surgically implanted. The left sciatic nerve of methoxyflurane-anesthetized female CD-1 mice (Charles River, Wilmington, MA) was exposed through an incision along the anterior-medial aspect of the upper thigh. A 4 mm segment of nerve proximal to the tibio-peroneal bifurcation was resected and discarded. A 4 mm nerve gap was created by anchoring the proximal and distal nerve stumps 4 mm apart within 6 mm long positively or negatively poled or unpoled PTFE tubes using single 10-0 nylon sutures. The PTFE tubes were prefilled with physiologic saline in order to prevent trapping of air bubbles within their lumens. Cohorts of 5 animals were implanted with PTFE electret tubes and control PTFE tubes (not submitted to electrical poling).

EXAMPLE 3

The guidance channels were recovered after 4 weeks of implantation. The mice were deeply anesthetized with Nembutal and then perfused transcardially with 5 ml of heparanized phosphate-buffered saline (PBS), followed by 10 ml of a fixative containing 3.0% paraformaldehyde, 2.5% glutaraldehyde, pH 7.4. The operative site was reopened, and the guidance channel and native sciatic nerve removed.

EXAMPLE 4

The recovered specimens were postfixed in a 1.0% osmium tetroxide solution, dehydrated, and embedded in Spurr resin. Transverse sections taken at the midpoint of the guidance channel were cut on a Sorvall MT-5000 microtome (E. I. Dupont DeNeneus & Co. Wilmington, Del.). Semi-thin and ultra-thin sections were stained and prepared for light and electron microscopy.

FIG. 2 shows toluidine blue-stained transverse sections of nerve regenerated at the midpoint of unpoled (A, B), negatively poled (C, D), and positively poled (E, F) PTFE tubes 4 weeks post-implantation. There were numerous myelinated axons surrounded by a fine epineurial sheath in poled tubes. Macrophages are often noted lining the regenerated cables and the inner wall of the guidance channel. Presumptive Schwann cells and numerous microfascicles surrounded by perineurial-like tissue, and numerous unmyelinated axons and myelinated axons at various stages of myelination, can also be observed. Several mast cells are seen within the regenerated cable.

EXAMPLE 5

The cross-sectional area of the regenerated cable, the total blood vessel area, and the number of myelinated axons and blood vessels were measured with a Zeiss IM 35 microscope interfaced with a computerized morphometric system (CUE-2, Olympus, Lake Success, NY). The Mann-Whitney rank sum test was used to assess statistical difference between the various populations.

TABLE 1

|  | Channel Type | | |
| --- | --- | --- | --- |
|  | Positive | Negative | Unpoled |
| Cable Area ($\times 10^4 \mu m^2$) | 16.7 +/− 1.5 | 12.5 +/− 1.4 | 10.2 +/− 1.2 |
| Number Myelinated Axons | 2,301 +/− 206 | 2,118 +/− 181 | 1,544 +/− 160 |

The cross-sectional area of nerves regenerated in positive poled PTFE channels was significantly greater than nerves regenerated in negatively poled and unpoled PTFE channels, as shown above in Table 1 and in FIG. 2. Cables regenerated in negatively poled channels were larger than those regenerated in unpoled channels, although the difference was not statistically significant. The ratio of blood vessel area to total cable area was greater in both poled channels as compared to unpoled channels (Table 1). The number of myelinated axons regenerated in positively and negatively poled channels was significantly greater than the number seen in unpoled channels but were similar to one another. Qualitatively, the geometry of the myelinated axons regenerated in both types of poled channels appeared to be more similar to those seen in normal nerves than those in unpoled channels.

We claim:

1. A method for preparing a medical device for use in the regeneration of a severed nerve, said method comprising the steps of:
    fabricating a tubular, biocompatible, polymeric membrane from a polymer having a polarizable membrane structure, said membrane having a lumen with a diameter of about 0.5 mm to 3.0 cm, and having openings adapted to receive the ends of said severed nerve and defining a lumen through which said nerve may regenerate; and
    poling said membrane to produce a quasi-permanent electric charge on an inner surface of said tubular membrane.

2. The method of claim 1 wherein said fabricating step further includes fabricating a biocompatible, polymeric, tubular membrane from polytetrafluoroethylene.

3. The method of claim 1 wherein the poling step further includes producing a quasi-permanent, positive charge on the inner surface of said tubular membrane.

4. The method of claim 1 wherein the poling step further includes producing a quasi-permanent, negative charge on the inner surface of said tubular membrane.

5. The method of claim 1 wherein the step of electrically poling said polymer further comprises producing a quasi-permanent, electric charge on the outer surface of said tubular membrane.

6. The method of claim 5 wherein the poling step further includes producing a quasi-permanent, positive charge on the outer surface of said tubular membrane.

7. The method of claim 5 wherein the poling step further includes producing a quasi-permanent, negative charge on the outer surface of said tubular membrane.

* * * * *